US007530944B1

(12) United States Patent
Kain

(10) Patent No.: US 7,530,944 B1
(45) Date of Patent: May 12, 2009

(54) EROGENIC STIMULATOR

(76) Inventor: Melissa Mia Kain, 1525 State Rd. 37 North, Mulberry, FL (US) 33860

(*) Notice: Subject to any disclaimer, the term of this patent is extended or adjusted under 35 U.S.C. 154(b) by 0 days.

(21) Appl. No.: 12/048,363

(22) Filed: Mar. 14, 2008

(51) Int. Cl.
*A61F 5/00* (2006.01)

(52) U.S. Cl. ........................................... 600/38; 600/41

(58) Field of Classification Search .............. 600/38–41
See application file for complete search history.

(56) References Cited

U.S. PATENT DOCUMENTS

| | | | | |
|---|---|---|---|---|
| 2,899,957 A | | 8/1959 | Briggs | |
| 5,127,396 A | | 7/1992 | McAllister | 600/38 |
| D384,156 S | | 9/1997 | Kain | D24/200 |
| 5,690,603 A | | 11/1997 | Kain | 600/38 |
| 5,693,002 A | * | 12/1997 | Tucker et al. | 600/38 |
| 6,099,463 A | * | 8/2000 | Hockhalter | 600/38 |
| 6,464,653 B1 | * | 10/2002 | Hovland et al. | 601/7 |
| 6,733,438 B1 | * | 5/2004 | Dann et al. | 600/38 |

* cited by examiner

*Primary Examiner*—John P Lacyk
(74) *Attorney, Agent, or Firm*—Robert C. Kain, Jr.

(57) ABSTRACT

The erogenic stimulator includes a first resilient end region (phallic) extending from a base and a second resilient bulbous end region extending therefrom. The bulbous end is connected via a reduced diameter neck to the base. The base and first and second ends form a truncated substantially U-shaped stimulator. A concave suction element is formed on the base in the curved portion of the U-shape. A passageway may be included from the concave suction element through the base into which may be inserted either a plug or a vibratory element. The plug/vibratory element closes the base end of the passageway thereby permitting expansion and contraction of the passageway dependent upon a predetermined condition at the suction opening of the passageway. If the suction element contacts the skin or an erogenous region and blocks the passageway, the rocking stimulator suctions and evacuates, alternatively, air through the suction opening of the passageway.

21 Claims, 2 Drawing Sheets

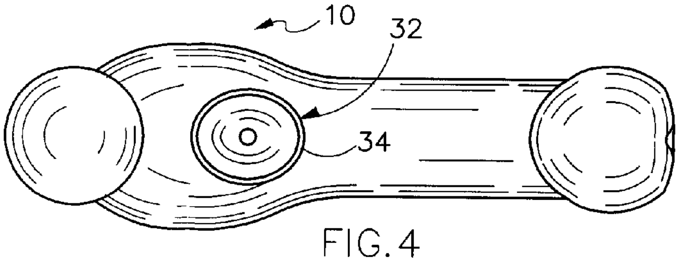
FIG.4
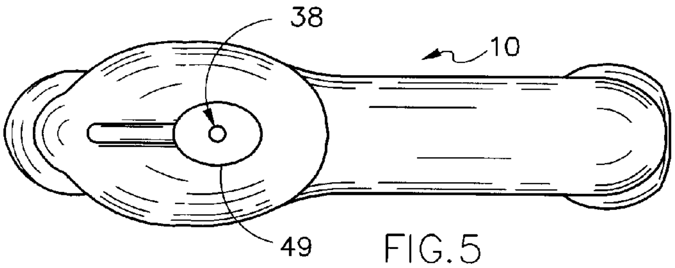
FIG.5
FIG.1C
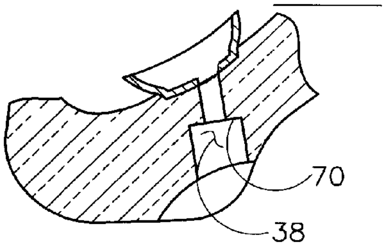
FIG.1E
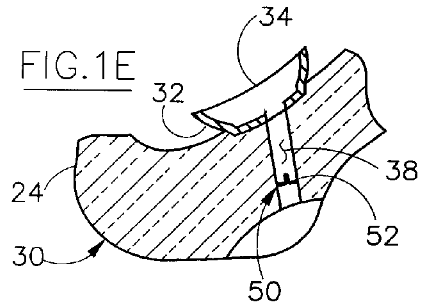
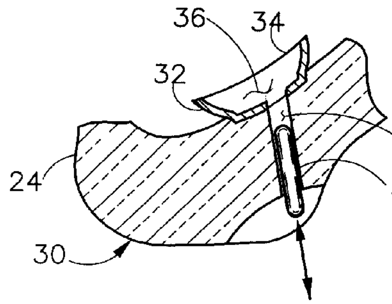
FIG.1B
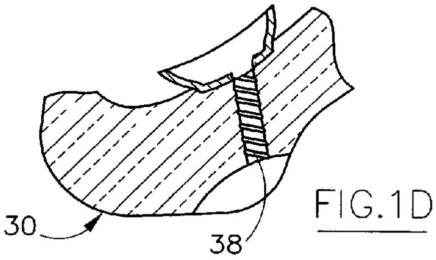
FIG.1D

EROGENIC STIMULATOR

The present invention relates to an erogenic stimulator with a suction cup and optionally with an associated chamber for either suction control or insertion of a vibrating unit.

BACKGROUND OF THE INVENTION

This invention pertains to sexual or erogenous stimulation devices in general and, more particularly, to a self-retained device for simultaneous use by two sexual partners such that the erotic areas of both such users are concurrently excited.

GENERAL BACKGROUND

Marital or sexual aids have been known and used throughout the centuries. Generally, such aids have been designed either for self-stimulation or for the stimulation of one party only. However, some aids satisfy two partners at the same time. This latter type of aid or stimulators is designed primarily for use by a female user and often incorporates a flexible phallic shaped stimulator secured to a base. Variations of this type of stimulator include two such phallic shapes linearly secured to opposite sides of a common or intermediate flange. Unfortunately, because of the co-linear nature of these opposite shapes, the simultaneous use of such a device by two partners requires some gymnastic-like maneuvers.

Also, it is common for these devices to not be self-retaining, that is, when one end is retained in the vagina or anal cavity, the other end is free to stimulate of the other person. Instead, these devices rely upon a series of straps in order to hold and retain the device in place on one user for proper use on the other person. However, fastening such straps prior to use is cumbersome and discomforting and causes undesirable delay.

U.S. Pat. No. 5,690,603 to Kain discloses a self-retaining stimulator, that is, when one end is retained in the vagina or anal cavity, the other end is free to stimulate the other person.

OBJECTS OF THE INVENTION

It is thus an object of the present invention to provide a marital or sexual aid that is capable of simultaneously stimulating the erotic areas of both users.

It is a further object of this invention to provide an aid that is self-retaining such that straps or other holding devices are not required, thereby eliminating any delay and discomfort.

A further object of this invention is to provide a device that is capable of being used by partners of the same sex or of the opposite sex.

Still another object of this invention is to provide a device that is capable of flexing as needed but which returns to its original position upon its release.

Yet another object of this invention is to provide an aid that is smoothly contoured for comfort.

An additional object is to stimulate the clitoris of one of the users with a suction element during sexual play with the stimulator.

A further object of the present invention is to develop a suction chamber which co-acts with the suction element thereby enhancing the sexual play with the stimulator.

SUMMARY OF THE INVENTION

In one embodiment, the erogenic stimulator includes a first elongated, resilient, cylindrical end region (typically a phallic shape) with a first end extending from a proximal base end and a second resilient, cylindrical, bulbous end region also extending from a proximal base end. The bulbous distal end is connected via a reduced diameter neck to that base. The base is further connected to the first end region. The base, the first phallic end and the second bulbous end extend upwards from the base forming a truncated substantially U-shaped stimulator. The stimulator includes a concave suction element on the base in a curved portion of the truncated U-shape. Other features include: a passageway from that bottom of the concave suction element through said base, into which may be inserted either a plug or a vibratory element. The plug/vibratory element closes the base end of the passageway thereby permitting expansion and contraction of the passageway dependent upon a predetermined condition of the suction opening of the passageway. If the suction element contacts the skin or erogenous region of one user and the plug/vibratory element blocks the passageway, a rocking or undulation of the stimulator suctions and evacuates, alternatively, air through the suction opening of the passageway. This suction and evacuation of air further energizes the skin or erogenous region of the user. The base may have a cut-away for removal of the plug/vibratory element.

BRIEF DESCRIPTION OF THE DRAWINGS

Further objects of the present invention can be found in the detailed description of the preferred embodiments when taken in conjunction with the accompanying drawings in which:

FIG. 4 diagrammatically illustrates a top view of the stimulator; and

FIG. 5 diagrammatically illustrates a bottom view of the stimulator.

DETAILED DESCRIPTION OF THE PREFERRED EMBODIMENTS

The present invention relates to a erogenic stimulator or martial aid.

Figure 1A:
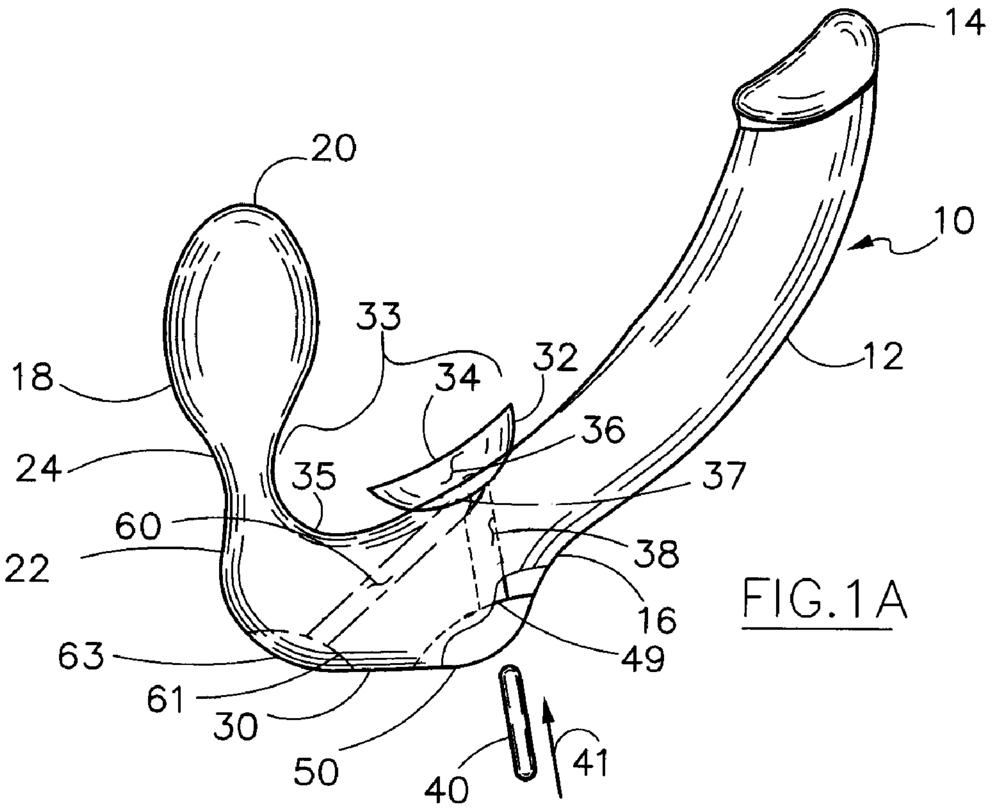
FIG. 1 diagrammatically illustrates a side elevational view of the erogenic stimulator aid including both the suction cup as well as the suction passageway and vibrator or closure plug.
FIG. 1B shows the removable plug or vibrating element to be disposed within the passageway.
FIG. 1C and FIG. 1D diagrammatically illustrate a stepped passageway and a treaded passageway.
FIG. 1E diagrammatically illustrates a one-way valve in the passageway.

Similar numerals designate similar items throughout the drawings and specification. FIG. 1A diagrammatically illustrates stimulator 10 having a first elongated, resilient and generally cylindrical end region 12. In the preferred embodiment, end region 12 has a phallic shape. First end region includes a first distal end 14 and a first proximal base end generally identified at end portion 16. Stimulator 10 includes a second resilient and generally cylindrical end region 18 sized for receipt in an anal or vaginal cavity. Second end region 18 includes a second bulbous distal end 20 and a second proximal base end generally near portion 22. This bulbous distal end 20 is connected via a reduced diameter neck portion or neck 24 between the bulbous end 20 and the second proximal base end 22. The second end region includes the bulbous element, the neck and the base end 22. Neck 24 enables bulbous end region 20 to flex thereat. Bulbous end 20 is adapted to permit the muscle groups of one of the partners using the stimulator to hold the second end in place during use. An alternative construct of the invention eliminates the neck and bulbous nature of second end 18.

Stimulator 10 includes a base 30 connected intermediate first proximal base end 16 and second proximal base end 22. First end region 12 and second end region 18 extend upwards from base 30 and forms a truncated, substantially U-shape stimulator. The U-shape is truncated since the second end region 18 is smaller in length then the first end region 12. Hence one of the legs of the U-shaped stimulator is truncated or shorter compared to the other leg. The U-shaped stimulator has a curved region 33. The U-shape of stimulator 10 may also be considered to be an L-shape due to the truncated nature of the bulbous end 18. The L-shape is rotated such that the intersection between the upper leg of the L-shape and the base of the L-shape is the location of the suction cup 32. Reference to a U-shaped stimulator is meant to cover an L-shaped stimulator herein.

A concave suction element 32 is mounted, attached or formed as part of the base in curved portion 33 of the truncated U-shape stimulator. Suction element 32 rises above or is formed on curve 33 of the U-shaped stimulator 10. Concave suction element 32 has a outer rim 34 rising above surface 35 of curve portion 33 of the truncated U-shape stimulator in the preferred embodiment. Outer rim 34 may be a circle, oval, ellipse, triangle, square, polygon, rectangle or a diamond shape. The suction element may have a low rise rim and be primarily formed by a depression in base 30.

Concave suction element 32 has an interior space 36. In one embodiment (an alternative embodiment), a passageway 38 leads from the base of interior 36 of suction element 32 and extends outboard or away from the suction element 32 and exits base 30 opposite curve portion 33 of the concave U-shape stimulator. Accordingly, passageway 38 has a first opening at the base of suction element 32 and a second opening on base 30 opposite curve region 33 of the truncated U-shape.

A removable plug or a vibrating element 40 is sized to fit snugly within passageway 38 and to extend either fully or partially into passageway 38 as shown by arrow 41 in FIG. 1A. In order to assist the user to remove or insert removable plug/vibrator element 40, base 30 may have a cut-away 50 about the second opening 49 of passageway 38. One type of small, cylindrical vibratory element is a MAGIC BULLET vibrator. Passageway 38 may extend at various angles from suction element 32. Auxiliary passageway 60 (an angled chamber) is shown in FIG. 1A with a dash-dot-dash line as an alternative route. Rather than a vertical passage, angled passageway 60 also works. Passageway 60 has an opening 61 generally opposite curved portion 33 of truncated U-shaped stimulator 10. A cut-away 63 may also be provided at opening 61 of chamber 60. Chamber 60 is sized to receive fully or partially a vibrating element. The vibratory element may be longer than passageway 38, 60. If the element slightly extends into the bottom of the suction element bowl 36, removal is easier.

FIG. 1B shows that removable plug 40 or vibrating element 40 has been partially inserted into passage 38.

In operation, one partner places bulbous distal end 20 in an anal or vaginal cavity and the first cylindrical end region 12, preferably having a phallic shape, is inserted into an anal or vaginal cavity of the other partner.

When removal plug or vibratory unit 40 is inserted into passageway 38, passageway 38 is partially closed. When in use, concave suction element 32 contacts the skin and erogenous zones of one of the partners. When suction element 32 (particularly rim 34) is in contact with skin or other erogenous body zone, and the stimulator 10 moves or rotates due to thrusting or rocking motion of one partner with respect to the other partner, suction is created and then released in truncated cavity 38 shown in FIG. 1B. Air is trapped when suction opening 37 is closed. If open, air is ejected from the passage. Thereafter upon close contact to the skin or erogenous zone, the passageway draws air therein enhancing the suction at element 32. Without the passageway 38, 60, suction is developed by flexing action of cup 32 on the skin or erogenous zone. Therefore, the suction element 32 enhances the sexual play of the users. The degree of suction is controlled by the inserted location of plug or element 40. The inclusion of a vibratory element 40 or a removable plug also affects the sexual play of the users. Cut-away 50 permits the plug to be removed or vibratory unit to be removed from chamber 38. The predetermined condition of the suction opening (or suction cup rim) depends upon an open or closed position with respect to the skin or erogenous zone.

FIG. 1C shows that passageway 38 with at least one step 70 which may be used to seal the vibratory unit or the removable part securely in the passageway. Multiple steps may be used. FIG. 1D shows that passageway 38 is threaded. The steps may provide a tactile indication of plug/vibrator depth.

FIG. 1E diagrammatically illustrates a one-way valve 50 in the passageway 38. The valve and valve stem 50 may be similar to the one-way valve and valve stem used on beach balls and other common manually inflatable items. The common valve and valve stem 50 extends from the distal end of passage 38. When cap 54 is withdrawn from the cap seat on the valve stem 56, air may flow out of passageway 38 due to compression at suction cup end 32, 34. The one way air valve 50 permits flow of air outbound from passage 38. One way valve 50 is opened when radial compression is applied to stem region 56, which compression opens valve 52 in the stem. Operationally, when the valve cap 54 is withdrawn from the valve stem seat, air may flow outboard of the passageway 38, but not inward into the passageway due to the one-way action of valve 52. When the cap is on the valve stem seat, air flow is generally prohibited.

Figure 2:
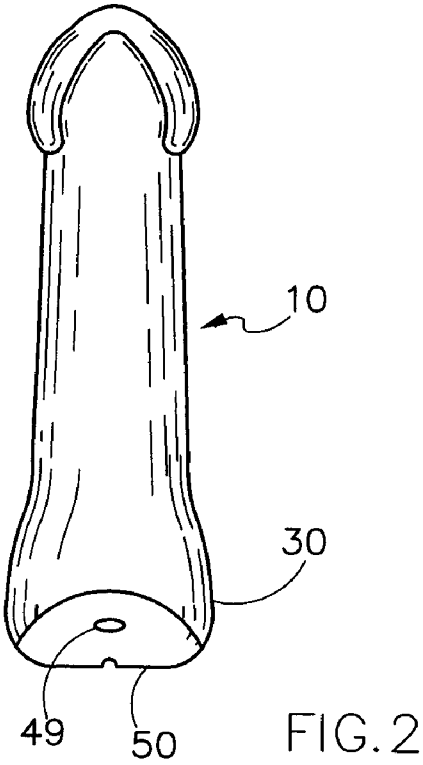
FIG. 2 diagrammatically illustrates a front elevational view of the erogenic stimulator.

FIG. 2 shows a front elevational view of stimulator 10 with cutout 50 in the base 30 and shows the location of exit opening 49 of passageway 38.

Figure 3:
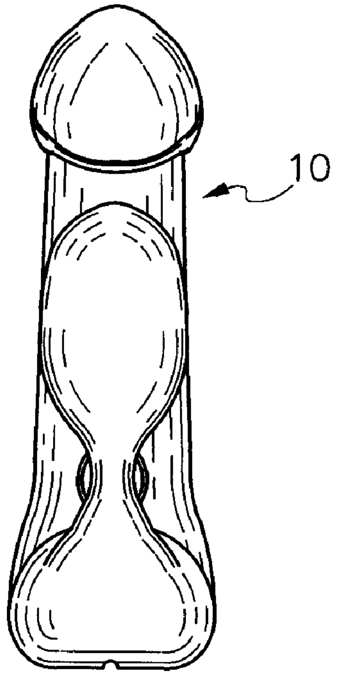
FIG. 3 diagrammatically illustrates a rear elevational view of the stimulator.

FIG. 3 shows a rear view of stimulator 10.

FIG. 4 is a top view showing stimulator 10 and generally round or oval rim 34 of suction element 32.

FIG. 5 is a bottom view of stimulator 10 shown through passage 38.

Stimulator 10 may be constructed of a rather rigid material such as hard plastic, rubber, or the like. However, it is preferable for stimulator 10 to be constructed of a more compressible or resilient material, such as soft plastic or a foam material, of the type that is capable of retaining its shape and rigidity during use, but which is not so un-bending or inflexible as to be uncomfortable. Silicone is a good material to use. Also, an outer continuous covering or coating which is both smooth and slippery over such material would further enhance the enjoyment of stimulator 10. Preferably, stimulator 10 is a unitary item wherein the base, the first end region and the bulbous second end region are all one piece and all made of the same flexible resilient material. Finally, it is anticipated that the angles of the legs of the truncated U-shape, that is, the general angle between the phallic end and bulbous end, would be in the range of from 60 to 80 degrees, more or less, so as to provide the most comfort during use, however, such angle may be as sharp as 45 degrees or as great as 90 degrees in some instances.

Of course, the actual length and diameter of phallic end and bulbous end can vary as needed depending on the needs of the partners. In this fashion, it is anticipated that different sizes of these ends can be offered which correspond with different sizes of the suction element and the neck portion or region so that stimulator 10 can conform to the needs and comfort levels of the intended users. The base at the curved region of the truncated U-shape may be larger or smaller than shown in relation to the phallus end and the bulbous end.

The claims appended hereto are meant to cover modifications and changes within the scope and spirit of the present invention.

What is claimed is:

1. An erogenic stimulator for use by two partners comprising:

a first elongated, resilient and generally cylindrical end region having a first distal end and a first proximal base end;

a second resilient and generally cylindrical end region sized for receipt in an anal or vaginal cavity, said second end region having a second bulbous distal end and a second proximal base end, said second bulbous distal end connected via a reduced diameter neck portion between the second bulbous distal end and said second proximal base end, said second end region being shorter than said first end region, said neck portion adapted for permitting the muscle groups of one of said partners to hold said second end region in place during use;

a base connected intermediate said first and second proximal base ends of said first and second end regions and said first and second end regions extending upwards from said base forming a truncated substantially U-shaped stimulator;

a concave suction element on said base in a curved portion of said truncated U-shape; and a passageway from said concave suction element through said base, said passageway having a first and second openings, said first opening formed within said suction element and said second opening being opposite said first opening and being outboard and away from said suction element.

2. An erogenic stimulator as claimed in claim 1 wherein said concave suction element has an outer rim raised above said base of said truncated U-shape, said rim shaped as a circle, an oval, an ellipse, a triangle, a square, a polygon, a rectangle or a diamond.

3. An erogenic stimulator as claimed in claim 1 wherein said passageway extends from a bottom of said concave suction element through said base, said second opening being opposite said curved portion of said truncated U-shape.

4. An erogenic stimulator as claimed in claim 1 wherein said first and second end region and said base are made of the same material and said first and second end region and said base are a single, unitary structure.

5. An erogenic stimulator as claimed in claim 4 wherein said material of said single, unitary structure is resilient, the stimulator includes a removable plug removably inserted into said passageway such that, when said plug is present in said passageway, said passageway expands and contracts dependent upon a predetermined condition of said first opening at said suction element.

6. An erogenic stimulator as claimed in claim 1 including a vibrating element sized to extend into said passageway.

7. An erogenic stimulator as claimed in claim 6 wherein a base portion proximate said second passageway opening has a cut-away for removal of said vibrating element.

8. An erogenic stimulator as claimed in claim 6 wherein said passageway is threaded or stepped therein.

9. An erogenic stimulator as claimed in claim 5 wherein a base portion proximate said second passageway opening has a cut-away for removal of said plug.

10. An erogenic stimulator as claimed in claim 9 wherein said passageway is threaded or stepped therein.

11. An erogenic stimulator as claimed in claim 1 wherein said passageway is an elongated angle chamber in said base, said second opening being opposite said curved portion of said truncated U-shape said stimulator including a vibratory element sized to extend into said angled chamber.

12. An erogenic stimulator as claimed in claim 11 including a cut-away about said chamber opening.

13. An erogenic stimulator as claimed in claim 1 including a one-way valve in said passageway.

14. An erogenic stimulator as claimed in claim 13 wherein said one-way valve includes a valve stem extending outboard of said second opening of said passageway and said base including a cut-away proximal said vale stem.

15. An erogenic stimulator for use by two partners comprising:

a first elongated, resilient and generally cylindrical end region having a phallic shape with a first distal end and a first proximal base end;

a second resilient and generally bulbous end region sized for receipt in an anal or vaginal cavity, said second end region having a second distal end and a second proximal base end, said bulbous end region connected via a reduced diameter neck between said bulbous end region and said second proximal base end, said second end region being shorter than said first end region, said neck adapted for permitting the muscle groups of one of said partners to hold said second end region in place during use;

a base connected intermediate said first and second proximal base ends of said first and second end regions and said first and second end regions extending upwards from said base forming a truncated substantially U-shaped stimulator;

a concave suction element on said base in a curved portion of said truncated U-shape; and a passageway from said concave suction element through said base, said passageway having a first and second openings, said first opening formed in said suction element and said second opening being opposite said first opening and being outboard and away from said suction element.

16. An erogenic stimulator for use by two partners comprising:

a first elongated, resilient and generally cylindrical end region having a phallic shape with a first distal end and a first proximal base end;

a second elongated, resilient and generally cylindrical end region sized for receipt in an anal or vaginal cavity, said second end region having a second distal end and a second proximal base end, said second end region being shorter than said first end region;

a base connected intermediate said first and second proximal base ends of said first and second end regions and said first and second end regions extending upwards from said base forming a truncated substantially U-shaped stimulator;

a concave suction element on said base in a curved portion of said truncated U-shape; and a passageway from said concave suction element through said base, said passageway having a first and second openings, said first opening formed within said suction element and said second opening being opposite said first opening and being outboard and away from said suction element.

17. An erogenic stimulator as claimed in claim 16 wherein said concave suction element has an outer rim raised above said base of said truncated U-shape, said rim shaped as a circle, an oval, an ellipse, a triangle, a square, a polygon, a rectangle or a diamond.

18. An erogenic stimulator as claimed in claim 16 wherein said second opening is opposite said curved portion of said truncated U-shape.

19. An erogenic stimulator as claimed in claim 16 wherein said base is made of resilient material, the stimulator includes a removable plug or vibratory unit removably inserted into said passageway such that, when said plug or vibratory unit is present in said passageway, said passageway expands and contracts dependent upon a predetermined condition of said first opening at said suction element.

20. An erogenic stimulator as claimed in claim 19 wherein a base portion proximate said second passageway opening has a cut-away for removal of said plug or vibratory element.

21. An erogenic stimulator as claimed in claim 20 wherein said passageway is threaded or stepped therein.

* * * * *